US008945023B2

(12) United States Patent
Mondro et al.

(10) Patent No.: US 8,945,023 B2
(45) Date of Patent: Feb. 3, 2015

(54) ELECTRODE LAYOUT FOR BLOOD TEST SENSOR STRIP

(71) Applicants: Jason Mondro, Sparta, NJ (US); David Schiff, Highland Park, NJ (US); Scott W. Gisler, Washingtonville, NY (US)

(72) Inventors: Jason Mondro, Sparta, NJ (US); David Schiff, Highland Park, NJ (US); Scott W. Gisler, Washingtonville, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/284,922

(22) Filed: May 22, 2014

(65) Prior Publication Data

US 2014/0251837 A1 Sep. 11, 2014

Related U.S. Application Data

(62) Division of application No. 12/689,654, filed on Jan. 19, 2010, now Pat. No. 8,771,202.

(51) Int. Cl.
| | | |
|---|---|---|
| *A61B 5/00* | (2006.01) | |
| *B65D 81/00* | (2006.01) | |
| *G01N 27/327* | (2006.01) | |
| *A61B 5/145* | (2006.01) | |
| *A61B 5/1477* | (2006.01) | |
| *A61B 5/1486* | (2006.01) | |
| *A61B 5/15* | (2006.01) | |

(52) U.S. Cl.
CPC ........ *G01N 27/3272* (2013.01); *A61B 5/14532* (2013.01); *A61B 5/1477* (2013.01); *A61B 5/1486* (2013.01); *G01N 27/3271* (2013.01); *A61B 5/1411* (2013.01); *A61B 2562/0209* (2013.01); *A61B 2562/0295* (2013.01); *A61B 2562/046* (2013.01); *A61B 2562/125* (2013.01)
USPC .......................................... 600/583; 600/584

(58) Field of Classification Search
USPC .......... 600/573, 575, 583, 584; 606/181, 182; 204/400, 403.01, 403.02, 403.03
See application file for complete search history.

(56) References Cited

U.S. PATENT DOCUMENTS

| | | | |
|---|---|---|---|
| 5,407,554 | A | 4/1995 | Saurer |
| 5,437,999 | A | 8/1995 | Diebold et al. |
| 5,741,634 | A | 4/1998 | Nozoe et al. |
| 6,143,164 | A | 11/2000 | Heller et al. |
| 6,558,402 | B1 | 5/2003 | Chelak et al. |
| 6,881,578 | B2 | 4/2005 | Otake |
| 6,893,545 | B2 | 5/2005 | Gotoh et al. |
| 7,192,405 | B2 | 3/2007 | DeNuzzio et al. |

(Continued)

FOREIGN PATENT DOCUMENTS

| | | |
|---|---|---|
| CN | 101400780 A | 4/2009 |
| WO | 03/093494 A2 | 11/2003 |
| WO | 2009/031313 | 3/2009 |

OTHER PUBLICATIONS

Communication pursuant to Article 94(3) EPC for European Patent Application 11151313.1 (Jul. 1, 2013).

(Continued)

*Primary Examiner* — Adam Eiseman
(74) *Attorney, Agent, or Firm* — Alan W. Fiedler; Fitzpatrick, Cella, Harper & Scinto

(57) ABSTRACT

An improved electrode layout for a continuous strip sensor is provided which reduces misalignment of the electrodes with the contacts which read the position of the strip. Better contact with the electrodes reduces or eliminates transient signals between stop positions of the sensor strip.

9 Claims, 4 Drawing Sheets

(56) References Cited

U.S. PATENT DOCUMENTS

| | | |
|---|---|---|
| 7,498,132 B2 | 3/2009 | Yu et al. |
| 2002/0177788 A1 | 11/2002 | Hodges et al. |
| 2002/0188224 A1 | 12/2002 | Roe et al. |
| 2006/0024774 A1 | 2/2006 | Zocchi |
| 2006/0064035 A1 | 3/2006 | Wang et al. |
| 2011/0015545 A1 | 1/2011 | Mondro |
| 2011/0015546 A1 | 1/2011 | Mondro et al. |

OTHER PUBLICATIONS

Extended European Search Report for European Patent Application 11151313.1 (Jun. 17, 2011).

FIG. 2

|    |         | 11                 | 21                        | 31                        | 41     |
|----|---------|--------------------|---------------------------|---------------------------|--------|
| 10 | Home    | Ground             | Unused                    | Ground                    | Ground |
| 14 | Lance   | Pressure Switch    | Unused (Lance Hole)       | Ground                    | Ground |
| 16 | Detect  | Top Detect Switch  | Ground                    | Bottom Detect Switch      | Ground |
| 18 | Acquire | Ground             | Rear Capillary Switch     | Front Capillary Switch    | Ground |

All Switches are Pulled High and Go to Ground When Shorted.

ELECTRODE LAYOUT FOR BLOOD TEST SENSOR STRIP

This application is a divisional of U.S. application Ser. No. 12/689,654, filed on Jan. 19, 2010, now U.S. Pat. No. 8,771, 202.

BACKGROUND OF THE INVENTION

1. Field of the Invention

The invention is in the field of blood sample acquisition and testing. In particular, the invention is directed to a sensor strip used in a device that performs both a lancing operation to acquire a blood sample and a measurement operation on the sample in one user-initiated step. The strip is provided with a plurality of test sites, and may be wound on a supply wheel and fed through the device between the supply wheel and a take-up wheel, so that a single strip may be used to obtain a plurality of measurements.

2. Description of the Related Art

Self-monitoring of blood glucose generally requires the user to extract a volume of capillary blood and place it on a disposable element for analysis. Devices for lancing a subject at an extraction site to obtain a small quantity of blood for testing on a test strip are known in the prior art. For example, U.S. Pat. No. 6,558,402, which is incorporated by reference, discloses a lancer having suitable mechanisms for piercing a subject's skin and obtaining a sample.

Test strip sensing elements using amperometric and other techniques for determining the concentration of blood glucose in a blood sample are known in the prior art. U.S. Pat. Nos. 6,143,164, and 5,437,999, incorporated by reference herein, each disclose examples of test strip construction for electrochemical measurement of blood glucose.

The integration of lancing and sensing would be a desirable advance in the self-monitoring of blood glucose. U.S. patent application Ser. No. 12/502,594, filed Jul. 9, 2009, describes such a "two-in-one" device, wherein a single test strip contains a plurality of test sites, which can be advanced automatically through a testing device. In this context, it would be desirable to have a layout of electrodes and contact pads on a test strip to permit automatic advancement of the strip through the device, that would account for variations in alignment, and to eliminate transient signals as the strip is indexed through different stop points in the lancing/sensing process and on to the next test position on the strip.

SUMMARY OF THE INVENTION

According to the present invention, an elongated sensor strip for use in a blood sample test device is provided comprising a plurality of test sites arranged in series in a travel direction on the strip. Each test site includes a lancet hole, electrodes for determining a blood sample volume, and test electrodes for determining a blood sample characteristic. Each test site on the strip comprises a non-conductive substrate layer and a conductive layer, which is formed into electrodes and conductive pads (such as by etching non-conductive lines in the conductive layer). The conductive pads are aligned with device contacts in the blood sample test device. A non-conductive layer is superposed on the conductive layer and has a window exposing a plurality of the conductive pads.

The conductive pads of the sensor strip are preferably formed by depositing a conductive layer and etching lines to form conductive pads in columns aligned with device contacts in a blood test device. Rows of the conductive pads correspond to stop positions in the lancing/sensing operation during which a blood sample is accumulated on the strip and then moved to a position where a blood glucose measurement is taken. Horizontal traces in the sensor strip which connect the electrodes on the strip with the conductive pads (which are perpendicular to the travel direction of the strip) are covered by a non-conductive cover layer, so that the horizontal traces are not directly contacted by the device contacts as the strip advances through the device.

A blood sample acquisition and sensing system according to the invention comprises a housing containing device contacts and the elongated strip having a plurality of test sites arranged in series in a travel direction on the strip, as described above. Each test site includes a lancet hole, electrodes for determining a blood sample volume, test electrodes for determining a blood sample characteristic, and conductive pads aligned in columns with the contacts on the blood test device for making electrical contact between the strip and the device contacts. The system also comprises a lancet and lancet injector, a motor for advancing the strip, and a processor. The processor is adapted to process signals produced when the device contacts make electrical contact with the conductive pads on the strip at stop positions in the lancing/sensing process, and to communicate with the lancet injector, the test electrodes, and the motor. In a preferred embodiment, the elements of the system, including the strip, lancet and lancet injector, motor and processor are provided in a unitary housing which may be provided with user-operable controls and a display.

A method for performing a plurality of blood sample acquisition and testing procedures on a strip according to the invention comprises the steps of: providing an elongated strip, such as described above, having a plurality of test sites arranged in series in a travel direction on the strip, wherein each test site includes a lancet hole, electrodes for determining a blood sample volume, test electrodes for determining a blood sample characteristic, and conductive pads for making electrical contact with a blood test sensor device; injecting a lancet through the lancet hole at a first test site into a subject to obtain a blood sample contacting the strip; contacting the blood sample with the electrodes for determining a blood sample volume so that a signal is produced when a blood sample volume is detected; advancing the strip responsive to the signal produced when a blood sample is detected; contacting the blood sample with the test electrodes to obtain a blood sample characteristic signal; and advancing the strip to a second test site.

BRIEF DESCRIPTION OF THE DRAWINGS

FIG. 2 depicts a matrix of showing the state of the electrodes at each stop position of the strip during the lancing/sensing process in an embodiment of the invention.

DETAILED DESCRIPTION OF THE PREFERRED EMBODIMENTS

Figure 1:
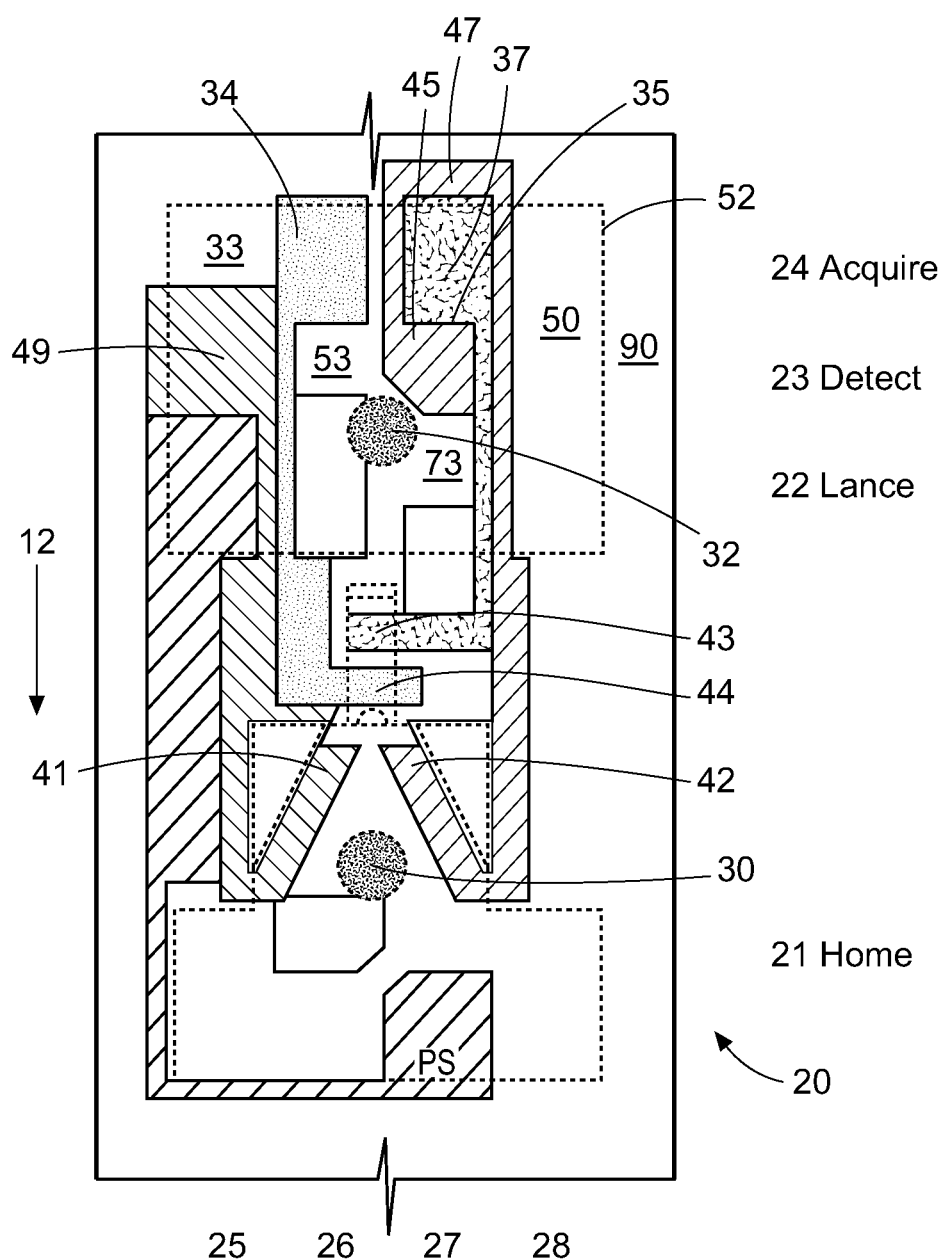
FIG. 1 depicts a test site on an elongated sensor strip according to an embodiment of the invention.

FIG. 1 schematically depicts a portion of an elongated sensor strip 20 according to an embodiment of the invention, including the elements found in a test site. A plurality of such test sites are provided in series along the travel direction 12 of the strip. Thus, each test site includes a lancet hole 30, electrodes 41, 42 for determining a blood sample volume, and test electrodes 43, 44 for determining a blood sample characteristic, all of which are arranged on a non-conductive substrate layer 50.

The material of the non-conductive substrate layer is not particularly limited and may be, for example, polyethylene terephthalate (PET) having a thickness in a range of about 5 mils to about 15 mils. The electrodes are preferably formed by sputtering a metal, such as gold, to form a conductive layer having a thickness in a range of about 50 Angstroms to about 2000 Angstroms, and etching a pattern to form the electrodes and conductive pads. Conductive pads, such as pad 45, are preferably formed from the same conductive layer by etching non-conductive lines, such as line 35. Other conductive materials and/or methods of depositing and/or patterning may be used. A non-conductive cover layer 90 forms a window, depicted by dotted line 52, exposing the pads to the contacts in the device as the strip is indexed through the device.

In a preferred embodiment, the horizontal traces, such as trace 47 between conductive pad 45 and electrode 42 are protected by the non-conductive cover layer 90 so that they are not severed by the device contact, and to minimize noise signals.

In a preferred embodiment, the leading edge of a first conductive pad, which is defined by a non-conductive line, is in front of a leading edge of another pad in the same row. In this way, the order in which signals are collected from the pads can be controlled. Thus, in each of rows 22, 23 and 24 (lance, detect, and acquire positions respectively); one contact has a shifted leading edge. For example, the leading edge of conductive pad 33 is behind the other pads in row 24 in respect of the travel direction, and is connected to the common ground. The leading edge of conductive pad 53 is behind pad 45 in row 23 and is connected to the common ground. Conductive pad 73 is behind the pressure switch pad PS in "lance" row 22. Pads 33, 53 and 73 are connected to a conductor at column 28, which is contacted by a grounding contact in the device to provide a reference. Column 28 is always grounded in the lance, detect, and acquire states represented by rows 22, 23 and 24. All of the conductive pads preferably have a surface area in a range of about 1.0 mm$^2$ to about 3.0 mm$^2$.

The structural layers of the test strip form features typical of an individual test strip, including a capillary channel and reagent wells. U.S. application Ser. Nos. 12/502,594 and 12/502,585, both filed Jul. 9, 2009 by the Assignee herein, and incorporated by reference herein, describe these details of the strip structure.

Figure 4A:
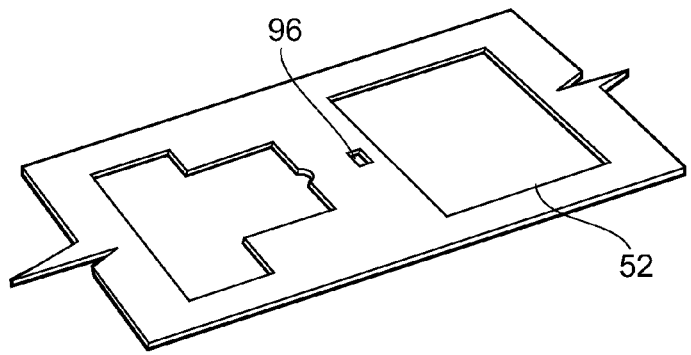
FIGS. 4A, 4B, 4C and 4D depict layers of the test strip, forming an exploded view of the structural features in a test site.
Figure 4B:
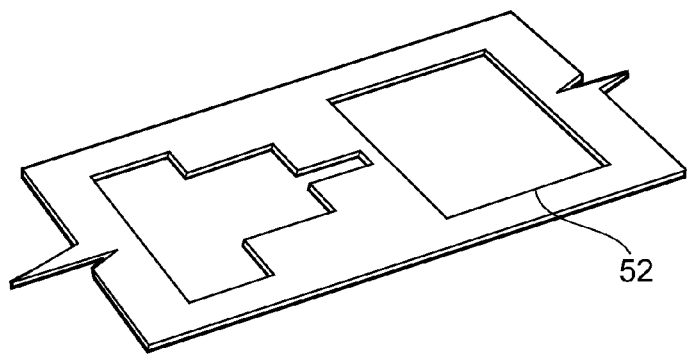
Figure 4C:
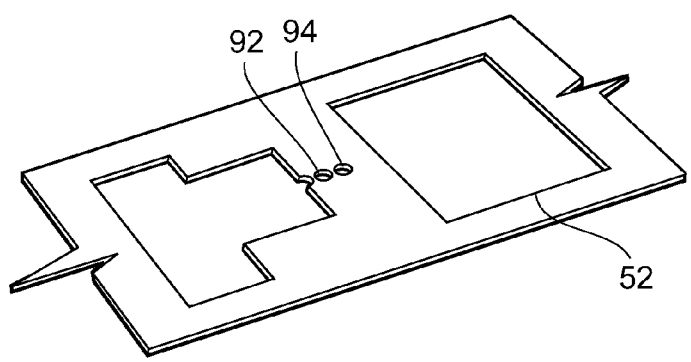
Figure 4D:
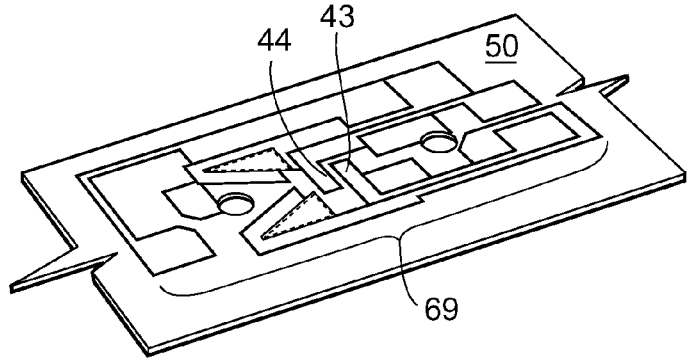

Referring to FIG. 4A through 4D, FIG. 4D shows non-conductive substrate layer 50 with a conductive pattern 69 of pads and traces formed thereon. FIG. 4C shows a non-conductive structural layer with the features of the reagent wells 92, 94 aligned with corresponding electrodes. FIG. 4B depicts a spacer layer which forms a capillary channel between the lancet hole and the wells. Top layer 4A forms vent 96. The top layer, spacer layer and structural layer share a window 52, which exposes conductive pads, but protects horizontal traces.

The conductive pads are arranged into columns 25, 26, 27, and 28, which are aligned with contacts in the device (not shown), which press against the sensor strip as it advances through the device. Rows of pads 21, 22, 23, and 24 correspond to positions of the tape in the lancing/sensing process. Lancet hole 30 is provided so that a lancet in the device can be injected through the hole into a subject's body. Sprocket hole 32 is provided in the strip so that a motor can control the advancement of the strip through the device in precise increments using a sprocket mechanism.

In the course of using the sensor strip, a lancet is injected through lancet hole 30 to obtain a blood sample. The blood sample is collected in the space between electrodes 41 and 42, which are connected by traces to conductive pads 49 and 45, respectively. When sufficient blood sample is accumulated, an electrical short is detected between electrodes 41 and 42, and a processor signals the motor to advance the strip in direction 12. Moving the strip causes the blood sample to be conducted to the test electrodes 43 and 44 at the bottom of corresponding reagent wells. Data from the electrochemical measurement of the blood glucose content of the sample is collected from signals generated by electrical contact made between device contacts and associated conductive pads 34 and 37. This information is routed to the processor for display, on the device housing or otherwise, and the sensor tape is thereafter advanced to the next test site on the strip so that the lancing/sensing process can be repeated.

FIG. 2 depicts a matrix which describes the state of the conductive pads at stop positions in the lancing/sensing process. The matrix comprises rows 10, 14, 16, and 18, and columns 11, 21, 31, and 41 corresponding to the conductive pads in an exemplary embodiment of the invention.

FIG. 2 depicts three active states and a home position. At the home position, depicted as row 10, first, third and fourth conductive pads are grounded and the second conductive pad is unused because it is not needed. This is the state of the device prior to conducting a lance operation. The device is not used in the home state. When the system is activated, the strip is positioned so that pressure sensor PS on the strip can be pressed against a subject's skin. This is the lance position of the strip, depicted as row 14, so that when the strip is in this position, the third and fourth contacts are grounded and the second contact is unused. At the lance position, the second contact is unused due to the presence of the lancet hole 30. At the detect position, in which a blood sample volume is detected, the second contact is grounded, the first contact is connected to the Top Detect Switch and the third contact is connected to the Bottom Detect Switch, represented in row 16 (i.e., the electrodes for determining a blood sample volume). When a blood sample creates an electrical short between electrodes 41 and 42 the switches in row 16 give the signal to the processor. At the acquire position, represented by row 18, the first contact is grounded, the second contact is connected to the "Rear Capillary Switch" and the third contact is connected to the "Front Capillary Switch," (i.e., the electrodes for determining a blood sample characteristic). The grounded contact is routed to the common ground in column 28, to minimize false readings. The signal for glucose reading produced by electrodes 43, 44 is sent to the processor through switches in row 18. Preferably, at least one of the test electrodes is active so that a current can be passed through the sample to obtain a blood glucose measurement.

The advancement of the strip is driven by a motor in response to commands from a processor. A control system stops the motor when a selected contact encounters the edge of a grounded electrode. The sensor strip may be wound on a supply wheel and taken up by a take-up wheel as the strip advances through the device. Sprocket holes 32 in the strip ensure that the motor advances the strip in controlled increments.

Figure 3:
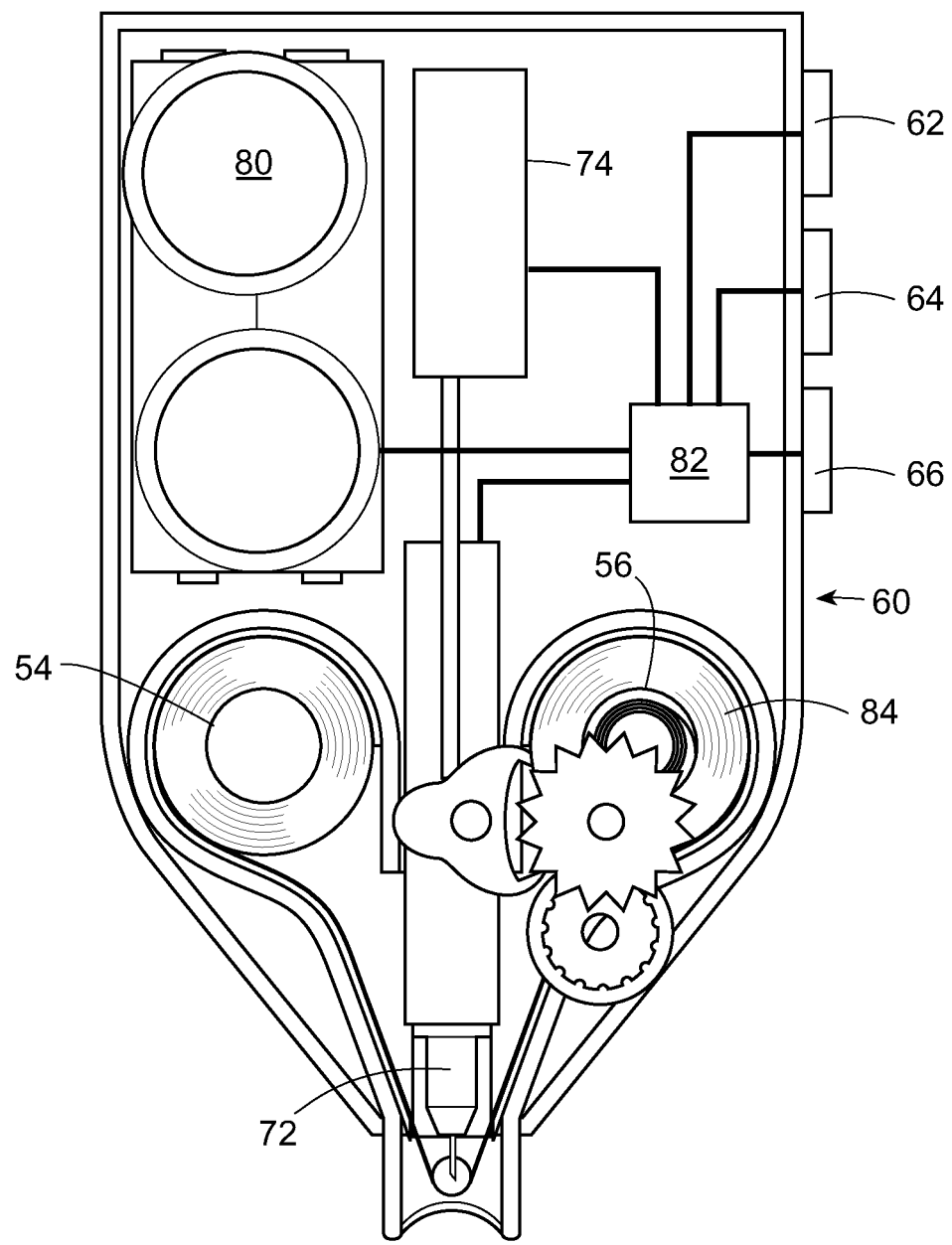
FIG. 3 depicts an embodiment of the system according to the invention, in which the sensor strip, lancet and processor are enclosed within a unitary housing.

As shown in an embodiment depicted in FIG. 3, a blood sample acquisition and sensing system may combine the elements described above in a unitary housing 60. Thus, an elongated sensor strip 84, having the features described above, may be provided to the housing on a supply wheel 54, and as the strip is advanced through the device, the sensor strip may be taken up on take-up wheel 56. Processor 82 communicates with a motor (not shown) to advance the strip, preferably using sprocket on the strip, so that the incremental advancement of the sensor strip is accurately controlled and not affected by the variation in the thickness of the layers of sensor strip being wound around the take-up wheel 56. The processor may communicate with user operable controls 64, 66, and a display 62 so that a user can conveniently control the system for self-monitoring of blood glucose. The elements are powered by any suitable power supply 80, such as a battery. The processor 82 communicates with lancet injector 74 to inject lancet 72 through the lancet hole on the strip.

The above description of the preferred embodiments should not be deemed as limiting the invention, which is defined by the following claims. Features described in the dependent claims are further aspects of the preferred embodiments, which may be used in combination.

What is claimed is:

1. A method for performing a plurality of blood sample acquisition and testing procedures on a strip
   having a plurality of test sites arranged in series in a travel direction on the strip, wherein each test site includes a lancet hole, first electrodes for producing a first signal when a sufficient volume of a blood sample is detected, second electrodes for obtaining a second signal characteristic of the blood sample, and a plurality of conductive pads that are aligned in a matrix of rows and columns and are aligned to make electrical contact with device contacts on a blood test sensor device, wherein the conductive pads for the first electrodes are electrically connected thereto by respective conductive traces, wherein the conductive pads for the second electrodes are electrically thereto by respective conductive traces, and wherein a leading edge in the travel direction of a first conductive pad in a row is in front of a leading edge in the travel direction of a second conductive pad in the same row, comprising the steps of:
   injecting a lancet through the lancet hole at a first test site into a subject to obtain the blood sample;
   contacting the blood sample with the first electrodes;
   advancing the strip in response to the first signal produced by the first electrodes;
   contacting the blood sample with the second electrodes to obtain the second signal; and
   advancing the strip to a second test site.

2. The method according to claim 1, wherein:
   at least three separate rows of conductive pads correspond to at least a lancing step position, a blood volume detection step position, and a blood characteristic sensing step position of the strip in a lancing/sensing process;
   at least four columns of conductive pads are aligned with respective device contacts; and
   at least two of the conductive pads in each said row are grounded at each of said positions in the lancing/sensing process.

3. The method according to claim 2, further comprising the step of
   producing a signal corresponding to a home position when electrical contact is made with conductive pads in a fourth row.

4. The method according to claim 1, further comprising the step of detecting the pressure of the strip against the subject prior to injecting the lancet into the subject.

5. The method according to claim 1, further comprising the step of obtaining the first signal when a blood droplet bridges a pair of first electrodes causing them to short.

6. The method according to claim 1, further comprising the step of passing current through the blood sample to obtain the second signal.

7. The method according to claim 1, wherein a non-conductive cover layer is provided over the conductive traces.

8. The method according to claim 6, wherein the second signal corresponds to an electrochemical measurement of blood glucose.

9. The method according to claim 7, wherein the non-conductive cover layer has a window to expose the conductive pads to the device contacts.

\* \* \* \* \*